| United States Patent [19] | [11] Patent Number: 4,544,506 |
|---|---|
| White et al. | [45] Date of Patent: Oct. 1, 1985 |

[54] QUATERNARY AMMONIUM COMPOUNDS AND METHOD FOR THEIR MANUFACTURE

[75] Inventors: Kenneth B. White, Chicago; James M. Richmond, Naperville; Keith D. Stanley, Downers Grove, all of Ill.

[73] Assignee: Akzona Incorporated, Enka, N.C.

[21] Appl. No.: 456,239

[22] Filed: Jan. 7, 1983

[51] Int. Cl.$^4$ .................. C07F 5/04; C07C 107/02
[52] U.S. Cl. ........................ 260/462 R; 564/294
[58] Field of Search ................. 260/462 R; 564/294

[56] References Cited

U.S. PATENT DOCUMENTS

| 3,772,357 | 11/1973 | Hamanaka | 260/462 R X |
|---|---|---|---|
| 4,136,039 | 1/1979 | Jäger et al. | 260/462 R X |
| 4,265,664 | 5/1981 | Saischek et al. | 260/462 R X |
| 4,376,736 | 3/1983 | Stanley | 260/462 R |
| 4,401,577 | 8/1983 | Richmond | 252/8.8 |

*Primary Examiner*—Helen M. S. Sneed
*Attorney, Agent, or Firm*—Francis W. Young; Louis A. Morris

[57] ABSTRACT

Quaternary ammonium compounds having the general formula:

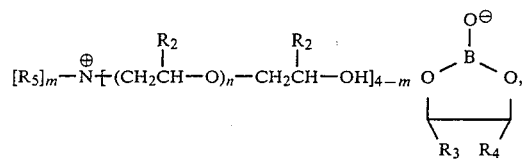

wherein m is either 0, 1, 2, or 3; each $R_5$ may be the same or different and are selected from the groups including straight- or branched-chain alkyl or alkenyl radicals having from 1 to 30 carbon atoms, inclusive, or a phenyl or benzyl radical; $R_2$ is H-, a $C_1$ to $C_{10}$ straight- or brached-chain alkyl or alkenyl radical, a phenyl group, a benzyl group, or a halogenated alkyl group; $R_3$ and $R_4$ are different or the same and are selected from the group including H-, or a $C_1$ to $C_{10}$ straight- or branched-chain alkyl or alkenyl radical, a phenyl group, or a benzyl group, and wherein n is an integer between 0 and 30, inclusive, and methods for their manufacture are described.

32 Claims, No Drawings

QUATERNARY AMMONIUM COMPOUNDS AND METHOD FOR THEIR MANUFACTURE

BACKGROUND OF THE INVENTION

The present invention relates to the preparation of novel quaternary ammonium compounds and particularly to alkoxylated quaternary ammonium alkylene glycol borate esters and methods for their preparation. The present compounds are alkoxylated at at least one and up to three of the quaternary nitrogen bonding sites.

The manufacture of alkoxylated quaternary ammonium alkylene glycol borate esters is unknown, although compounds comprised of an inorganic cation or an alkyl quaternary cation and this anion are known. Examples of such compounds include the sodium salt of a boric acid cyclic phenylethylene ester disclosed by Bell in the *Australian Journal of Chemistry*, volume 23, issue 7 (1970), pages 1415–1420 (Chem. Abstracts reference 65954r); and the quaternary ammonium glycol monoborate salts disclosed by Hunter in U.S. Pat. No. 3,169,983, issued Feb. 16, 1965.

The present alkoxylated quaternaries are found to be useful in the manufacture of polyurethane foams. In several U.S. Patents, including U.S. Pat. Nos. 3,661,809; 3,726,816; and 4,256,802, urethanes are manufactured by blending two components, stirring, and then allowing the blend to rise in an open container so as to form the desired foam. These two components are known as the "A" and "B" components, with the "A" component comprising the isocyanate and the "B" component comprising a blend of polyol, catalyst, surfactant, and blowing agent. All of the methods of polyurethane foam manufacture disclosed in the above patents, however, require that a conventional catalyst, such as an alkali metal salt, be used.

SUMMARY OF THE INVENTION

The present compounds are quaternary ammonium compounds having the formula:

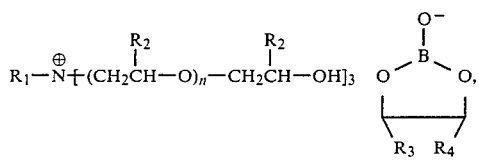

wherein $R_1$ is a straight- or branched-chain alkyl or alkenyl radical having from 1 to 30 carbon atoms, inclusive, or a phenyl or benzyl radical; $R_2$ is H-, a $C_1$ to $C_{10}$ straight- or branched-chain alkyl or alkenyl radical, a phenyl group, a benzyl group, or a halogenated alkyl group; $R_3$ and $R_4$ are different or the same and are selected from the group including H-, or a $C_1$ to $C_{10}$ straight- or branched-chain alkyl or alkenyl radical, a phenyl group, or a benzyl group, and wherein n is an integer between 0 and 30, inclusive, and methods for their manufacture are described.

In yet another embodiment of the invention, the alkylene glycol borate ester anion depicted hereinabove is coupled with the cationic moiety:

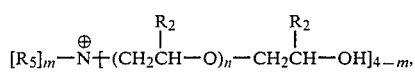

wherein m is either 0, 1, 2, or 3; each $R_5$ may be the same or different and are selected from the groups including straight or branched-chain alkyl or alkenyl radicals having from 1 to 30 carbon atoms, inclusive, or a phenyl or benzyl radical; $R_2$ is H-, a $C_1$ to $C_{10}$ straight- or branched-chain alkyl or alkenyl radical, a phenyl group, a benzyl group, or a halogenated alkyl group, and wherein n is an integer between 0 and 30, inclusive.

In another embodiment, the ethylene glycol borate ester anion depicted hereinabove is coupled with the cationic moiety:

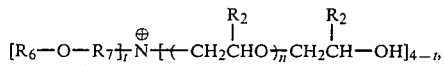

wherein n and $R_2$ are as defined hereinabove, t is either 1, 2, or 3, $R_6$ is a $C_1$–$C_{20}$ alkyl or alkoxy group, and $R_7$ is a $C_2$ or $C_3$ alkyl group. Preferably, $R_7$ is —$C_3H_6$— and $R_6$ is a combination of approximately equal amounts of $C_{12}$–$C_{15}$ alkyl groups.

The above compounds may be manufactured by a process in which boric acid is blended with an alkylene glycol, and then heating the blend. The water produced in the reaction is stripped off in successive atmospheric and vacuum distillation steps. Preferably, enough water is removed so that no more than 0.2% by weight remains in the alkylene glycol borate ester formed in the reaction. The dried borate ester is added to a primary, secondary, tertiary, or ether amine to form an aminated alkylene glycol borate ester. Finally, this aminated borate ester is alkoxylated with an alkylene oxide in the presence of a solvent.

The reaction of the glycol and boric acid may be represented as follows:

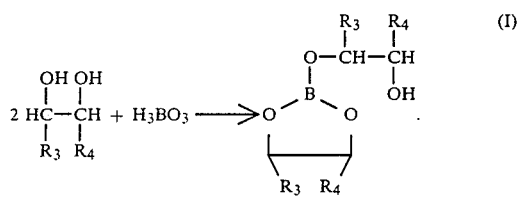

When the above ester is reacted with an amine, as for example a primary amine and 3 moles of ethylene oxide,

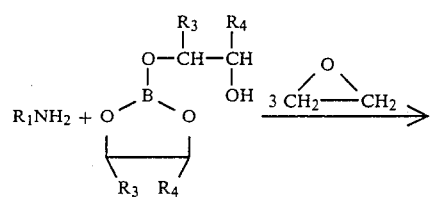

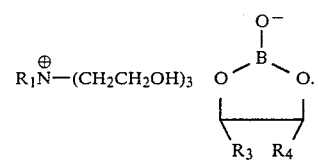

The remaining portion of the originally formed borate ester is cleaved away from the anionic portion and forms an alkylene oxide.

Accordingly, $R_3$ and $R_4$ in the present compounds may be modified by appropriate use of glycols in the first reaction with boric acid. For example, to attain the present compound wherein $R_3$ is H- and $R_4$ is $C_8$-, one should react 2 moles of 1,2-dihydroxy decane with a mole of boric acid.

For secondary amines, where $n=0$, 2 moles of the alkylene oxide are added per mole of amine. For $n>0$, the moles of alkylene oxide added will be $2(n+1)$ per mole of amine.

For any primary, secondary, or tertiary amine not having a hydroxyalkyl group thereon, and where n and m are as defined above, the required moles of alkylene oxide used will be moles alkylene oxides $=(n+1)(4-m)$, as will be recognized by those skilled in the art.

A still further embodiment of this invention is a method as disclosed above wherein the molar ratio of the alkylene glycol to boric acid is between 1:1 and 3:1. In another embodiment, the solvent comprises from 5% to 20% of the combined weight of all of the reactants, that is, the solvent, boric acid, alkylene glycol, amine, and alkylene oxide. In other embodiments, the molar ratio of the amine to the alkylene glycol borate ester is 1:1, and the solvents are selected from the group including diethylene glycol and ethylene glycol.

Suitable alkylene glycols may be selected from the group including ethylene glycol and propylene glycol. Further, it will be appreciated by those skilled in the art that any alkanol or other hydroxy-containing compound may be combined with boric acid to form a similar borate ester. Some suitable primary amines include tallowamine, 3-alkoxypropylamine, cocoamine, dodecylamine, and hexadecylamine. Secondary amines, among others, may be selected from the group including di(hydrogenatedtallow)amine and dicocoamine. Examples of some suitable tertiary amines are N-methyl diethanolamine, triethyl amine, dimethylethanolamine, and N,N-dimethyldodecyl-amine. Alkylene oxides may include ethylene oxide, propylene oxide, styrene oxide (for $R_2=C_6H_5$), 3-phenyl-1,2 propylene oxide (for $R_2=C_6H_5CH_2-$), and 4,4,4-trichloro-1,2-butylene oxide (for $R_2$ as a halogenated alkyl group), and suitable solvents include diethylene glycol, dipropylene glycol, ethylene glycol, 2-ethylhexanol, and any other alkanol, such as isopropyl alcohol, ethanol, and methanol.

DESCRIPTION OF THE PREFERRED EMBODIMENTS

The present compounds may be manufactured using equipment commonly available to those who manufacture conventional quaternary ammonium compounds.

The preferred method comprises charging an alkylene glycol and boric acid to a reactor, preferably including a distilling column upon which vacuum may be drawn. The glycol borate ester blend is heated to 120° C. at atmospheric pressure, and water will begin boiling off of the water-borate ester blend. Vacuum of 15–20" Hg is placed upon the column and a small amount of nitrogen is introduced into the reactor, both to assist in the removal of any remaining water. When the rate of distillation slows, the reactor is slowly returned to atmospheric pressure. Care should be taken not to use excessive vacuum, as the alkylene glycol borate ester boils at 120° C. at an absolute pressure of 1.5 to 2.0 mm Hg. The dried product is analyzed for water, and the distillation steps repeated until the water content is at or below 0.2%. The amine and the solvent are then transferred to an autoclave, as for example a Carpenter 20 autoclave, communicative with an alkylene oxide reservoir. The borate ester is added slowly, resulting in an exothermic reaction. The reactor is cooled so as to maintain the contents at from 75° C. to 85° C., and purged three times with nitrogen in successive pressure-vent cycles. The vent is then closed, and the reactor charged with nitrogen to 7 psig.

The alkylene oxide is then added with the reactor contents at 75° C. to 85° C. and at a rate such that the reactor pressure does not exceed 50 psig. When all of the alkylene oxide is charged, digestion thereof is allowed until the reactor pressure drops to 20–25 psig.

A conventional analysis of the total milliequivalents per gram (meq/g) of quat and free amine in the reaction mixture is then made. The "percent conversion" is defined as:

$$\left( \frac{\text{meq/g quat}}{\text{meq/g quat} + \text{meq/g free amine}} \right) \times 100.$$

If this percent conversion is less than 70%, additional alkylene oxide is added until the percent conversion exceeds 70%.

A Karl-Fischer water analysis is obtained on the remaining quat/free amine blend. If the water content is less than 0.1%, the reactor is vented, cooled to 75° C., and the reaction mixture removed therefrom. The resulting mixture primarily contains a compound in accordance with the present invention.

If the amount of water exceeds 0.1%, the reactor should be vented to 0 psig, then purged with nitrogen at a rate of 1.5 standard cubic feet per hour (1.5 SCFH) per pound of batch weight, maintaining the reactor at 100° C. This procedure is continued and the water content checked every two hours until it drops below 0.1% or until three consecutive analyses show no change. Finally, the reactor is vented, cooled to 75° C., and the contents discharged. The contents are primarily a compound in accordance with the present invention.

Specific examples are listed hereinbelow, which are the preferred methods of manufacturing the cited compounds in accordance with the above general procedure.

EXAMPLE 1

327 grams (5.27 gram moles) of ethylene glycol was added to 163 grams (2.63 gram moles) of boric acid in a one-liter, three neck flask equipped with a heating mantle, a Dean Stark trap, and a condenser. The mixture was heated to 120° C. at atmospheric pressure. After heating the mixture for about 1 hour 45 minutes at temperatures between 120° and 129° C., during which time about 45 grams of water was stripped off of the blend, a water aspirator was started so as to create a slight vacuum at the condenser. During the next three hours, a total of 83.4 additional grams of water were stripped for a total of 124.5 grams or 6.92 gram moles, which is 87.7% of the theoretical amount of 7.89 gram moles (3 moles water per mole boric acid). One hundred and seventy three (173) grams of the resulting adduct shown at Formula (I) was added to 327.7 grams (1.246 moles) of Armeen® TMD aliphatic amine in a 1 liter Parr Carpenter 20 autoclave (hereinafter "reactor"). Armeen® TMD aliphatic amine is available from the Armak Company, Industrial Chemicals Division, 300

South Wacker Drive, Chicago, Ill. 60606, and is commonly known as distilled grade tallowamine. After the amine and borate ester were blended, the autoclave was twice purged with nitrogen at 50 psig.

The reactor is communicative with an ethylene oxide reservoir through a stainless steel tube. Ethylene oxide, pressured in its reservoir by nitrogen, is slowly added to the reactor over the next 16 hours, at which time the reactor is at a pressure of 25 psig and 7.0 gram moles of ethylene oxide have been added. The resulting product is a ethoxylated quaternary ammonium ethylene borate ester having the formula:

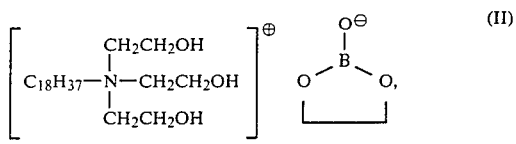

the $C_{18}H_{37}$ in the above-formula representing the primarily eighteen carbon tallow alkyl grouping. Upon analysis, the reaction mix was found to contain 3.5% free amine, 69.4% quaternary ammonium borate ester, and 1.2% water.

EXAMPLE 2

1500 grams of ethylene glycol (24.2 moles) were blended with 746.7 grams of boric acid (12.1 moles) to yield the borate ester shown at formula (I). The mixture was heated to 135° C. under slight vacuum so as to remove water therefrom, as in Example 1. To 134 grams of this borate ester (1.01 gram moles) in a reactor was added 265.6 grams (1.01 gram moles) of Armeen® T. Armeen® T is a product of the Armak Company, Industrial Chemicals Division, 300 South Wacker Drive, Chicago, Ill., 60606, and is commonly known as technical grade tallowamine. 252.5 grams (5.74 gram moles) of ethylene oxide are added at 50 psig and 75° C. over the next 8½–9 hours after the addition of 72.5 grams of diethylene glycol (a solvent), added so as to comprise 10% of the combined weight of the amine, the ethylene glycol borate ester, the ethylene oxide, and the solvent. The resulting product is that set forth above at formula (II). Analysis indicates that 24.3% of the reaction mixture is present as a free amine, whereas 39.0% of the mixture is a quaternized compound.

EXAMPLE 3

304 grams of 1,2-propane diol (4.0 gram moles) are added to 124 grams of boric acid (2.0 gram moles) in a one-liter, three neck flask equipped with a heating mantle, a Dean Stark trap, and a condenser. The mixture is heated to 128° C. at atmospheric pressure, and retained there for about 3½ hours, during which time about 44.5 grams of water are stripped from the mixture. A water aspirator is then started so as to create a slight vacuum at the condenser, and another 65.0 grams of water is stripped from the mixture during the next 5¾ hours. The total water removed of 109.5 grams corresponds to the stoichiometrical amount, but analysis of the adduct remaining in the flask showed that it contained 3.4% water.

160 grams (1.0 gram mole) of this propylene glycol borate ester are added to 262 grams (1.0 gram mole) of Armeen® TMD aliphatic amine and 134 grams (1.0 gram mole) of dipropylene glycol, a solvent. The reactor in which these reactants are blended is communicative with an ethylene oxide reservoir through a stainless steel tube. Four moles of ethylene oxide, pressurized in its reservoir by nitrogen, are slowly added to the reactor over the next 8½ hours, and the resulting quaternary is represented by the formula:

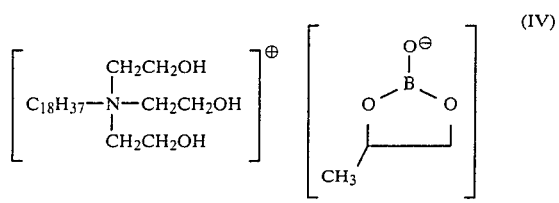

The product formed in the above ethoxylation comprises 48.6% of the ethoxylated quaternary ammonium borate ester shown above and 10.3% free amine.

EXAMPLE 4

Propylene glycol borate ester was prepared in accordance with the procedures set forth in the first paragraph of Example 3 hereinabove. 131.8 grams (0.824 gram moles) of this borate ester were blended with 230.1 grams (0.824 gram moles) of Armeen® EA 25 aliphatic amine and 40.9 grams diethylene glycol in a one liter, Carpenter 20 Parr autoclave. Armeen® EA 25 aliphatic amine is 3-alkoxypropylamine, and is available from the Armak Company. It is an ether monoamine made from an alcohol mixture comprised mainly of $C_{12}$–$C_{15}$ alcohols, approximately equal amounts of all chain lengths being present. The autoclave is communicative with an ethylene oxide reservoir through a stainless steel tube. After heating the reaction mixture to 72° C., 4.12 gram moles of ethylene oxide are added thereto over the next six hours. Upon analysis, the product formed by the ethoxylation proved to be:

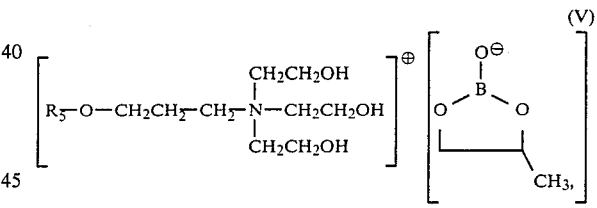

wherein $R_5$ comprises mainly $C_{12}$–$C_{15}$ alkyl groups, approximately equal amounts of all chain lengths being present. The final reaction mixture contained 2.0% free amine, 57.3% quaternary ammonium borate ester, and 0.5% water.

EXAMPLE 5

Ethylene glycol borate ester was prepared in accordance with the procedures set forth in the first paragraph of Example 1 hereinabove. 225.6 grams (1.70 gram moles) of this borate ester, 200 grams (1.70 gram moles) of N-methyl diethanol amine, a tertiary amine, and 143.8 grams of diethylene glycol are added to an autoclave that is communicative with an ethylene glycol reservoir through a stainless steel tube. Over the next five hours, 149.6 grams (3.40 gram moles) of ethylene oxide are added to the mixture in the autoclave, and the reaction mixture is then cooled and analyzed. Only 0.24% water remains in the quaternary ammonium borate ester. The resulting quaternary ammonium ethylene glycol borate ester has the structure:

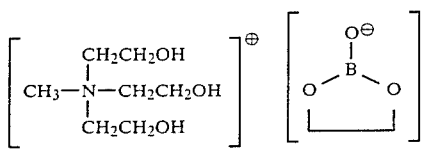

(VI)

EXAMPLE 6

Propylene glycol borate ester was prepared in accordance with the procedures set forth in the first paragraph of Example 3 hereinabove. 240.0 grams (1.50 gram moles) of this borate ester were blended in a one-liter, Carpenter 20 Parr autoclave with 151.8 grams (1.50 gram moles) triethyl amine and 92.2 grams of diethylene glycol, a solvent. The diethylene glycol is added in an amount sufficient so that it will comprise 15% of the total weight of solvent, borate ester, amine, and propylene oxide. After heating the reaction mixture to 75° C., propylene oxide is added slowly thereto until 130.7 grams (2.25 gram moles) have been added in six hours. Analysis of the resulting reaction mixture disclosed a compound having the formula:

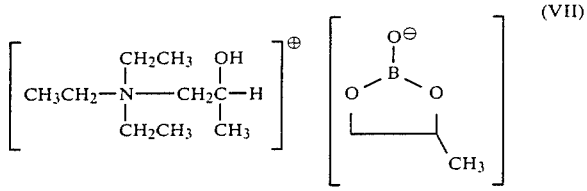

(VII)

The reaction mixture has a moisture of 0.14%.

EXAMPLE 7

Propylene glycol borate ester was prepared in accordance with the procedures set forth in the first paragraph of Example 3 hereinabove. 240.0 grams (1.50 gram moles) of this borate ester were blended in a one-liter, Carpenter 20 Parr autoclave with 151.8 grams (1.50 gram moles) triethyl amine and 80.7 grams of diethylene glycol, a solvent. This blend is heated to 75° C., and ethylene oxide is added slowly thereto until 66.0 grams (1.50 gram moles) have been added over 4½ hours. Analysis of the resulting reaction mixture disclosed a compound having the formula:

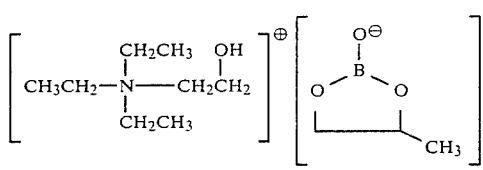

(VIII)

The product had a moisture content of 0.48%.

EXAMPLE 8

Propylene glycol borate ester was prepared in accordance with the procedures set forth in the first paragraph of Example 3 hereinabove. Eighty grams (0.5 gram moles) of this propylene glycol borate ester was blended with 131 grams (0.5 gram moles) of Armeen® TMD aliphatic amine and 26 grams of dipropylene glycol, a solvent, in a one liter, Carpenter 20 Parr autoclave. After heating the reaction mixture to 75° C., 2.0 gram moles (88 grams) of ethylene oxide are added thereto over the next 4½ hours. The resulting reaction mixture proved upon analysis to contain 53.4% of a quaternary, 9.7% free amine, and 1.0% water. The quaternary was of the formula:

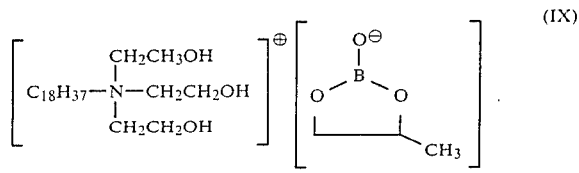

(IX)

EXAMPLE 9

Propylene glycol borate ester was prepared in accordance with the procedures set forth in the first paragraph of Example 3 hereinabove. Ninety five grams (0.63 moles) of this propylene glycol borate ester were blended with 125 grams (0.63 moles) of Armeen® C aliphatic amine and 25 grams of ethylene glycol, a solvent, in a one-liter Carpenter 20 Parr autoclave. Armeen® C aliphatic amine is the trademark of the Armak Company, Industrial Chemicals Division, for cocoamine. After heating the reaction mixture to 75° C., 3.15 gram moles (138.6 grams) of ethylene oxide are added thereto over the next 8¾ hours. Analysis of the resulting reaction mixture disclosed the presence of 3.4% free amine, 1.2% water, and 61.8% of an ethoxylated quaternary propylene glycol borate ester having the general formula:

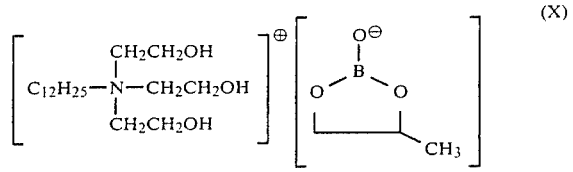

(X)

EXAMPLE 10

Propylene glycol borate ester was prepared in accordance with the procedures set forth in the first paragraph of Example 3 hereinabove. One hundred and fifty grams (1.0 gram mole) of this borate ester were blended with 262 grams (1.0 gram mole) of Armeen® TM 97 aliphatic amine and 52.4 grams of ethylene glycol, a solvent, in an autoclave. Armeen® TM 97 is the trademark for Armak's tallowamine, 97% primary amine. After heating the reaction mixture to 75° C., 5.0 gram moles (220 grams) of ethylene oxide are added thereto over the next 6¾ hours. The resulting reaction mixture proved upon analysis to contain 4.9% free amine and 57.4% of the quaternary having the formula:

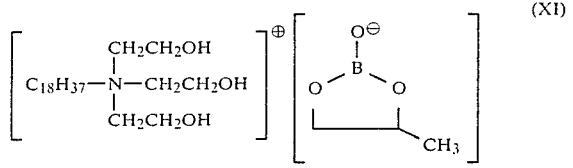

(XI)

EXAMPLE 11

Propylene glycol borate ester was prepared in accordance with the procedures set forth in the first paragraph of Example 3 hereinabove. 94.4 grams (0.59 gram moles) of this borate ester were blended with 300 grams (0.59 gram moles) of Armeen ® 2HT aliphatic amine, so as to obtain a 1:1 molar ratio of amine to borate ester, and 39.4 gram moles of diethylene glycol, a solvent. Armeen ® 2HT is the Armak Company's trademark for di(hydrogenated)tallowamine, a secondary amine. After heating the reaction mixture to 75° C., 2.95 gram moles (129.8 grams) of ethylene oxide are added thereto over the next 12½ hours. Analysis of the resulting mixture showed a blend containing 21.4% free amine and 65.5% quaternary ammonium borate ester having the formula:

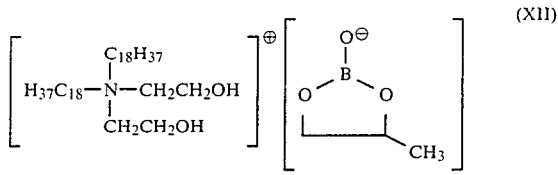

EXAMPLE 12

Propylene glycol borate ester was prepared in accordance with the procedures set forth in the first paragraph of Example 3 hereinabove. 134.4 grams (0.84 gram moles) of this propylene glycol borate ester were blended with 225 grams (1.125 gram moles) of Armeen ® C aliphatic amine, so as to obtain a 1:0.75 molar ratio of amine to borate ester, and 40.9 grams of diethylene glycol, a solvent, in an autoclave. After heating the reaction mixture to 75° C., 184.8 grams (4.2 gram moles) of ethylene oxide are added, thereto over the next 5¼ hours. Analysis of the resulting mixture showed a blend containing 25.3% free amine and 48.5% quaternary ammonium borate ester having the formula:

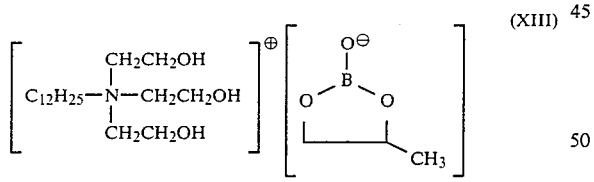

EXAMPLE 13

Propylene glycol borate ester was prepared in accordance with the procedures set forth in the first paragraph of Example 3 hereinabove. 62.4 grams (0.39 gram moles) of this borate ester were blended with 400 grams (0.78 gram moles) of Armeen ® 2HT aliphatic amine, so as to obtain a 1:0.5 molar ratio of amine to borate ester, and 41.3 grams of diethylene glycol, a solvent. After heating the reaction mixture to 75° C., 85.8 grams (1.95 gram moles) of ethylene oxide are added thereto over the next 4½ hours. Analysis of the resulting mixture showed a blend containing 40.1% free amine and 57.2% of a quaternary ammonium borate ester having the formula:

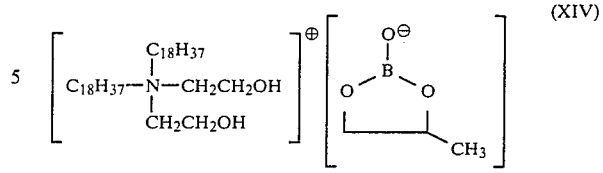

EXAMPLE 14

Propylene glycol borate ester was prepared in accordance with the procedures set forth in the first paragraph of Example 3 hereinabove. 40 grams (0.25 gram moles) of this borate ester were blended with 262 grams (1.0 gram mole) of Armeen ® TM 97 aliphatic amine, so as to obtain a 1:0.25 ratio of amine to borate ester, and 58.1 grams of diethylene glycol, a solvent. After heating the reaction mixture to 75° C., 121.0 grams (2.75 gram moles) of ethylene oxide are added thereto over the next 2¼ hours. Analysis of the resulting mixture showed a blend containing 45.4% free amine and 36.7% of a quaternary ammonium propylene glycol borate ester having the formula:

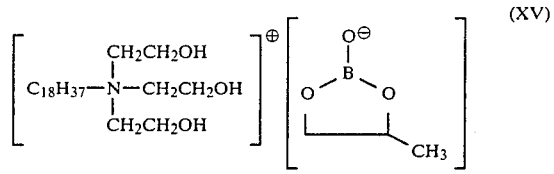

The results of Examples 11–14 are summarized in the following Table I:

TABLE I

CONVERSION TO QUATERNARY AMMONIUM COMPOUND USING VARIOUS MOLE RATIOS OF AMINE:PROPYLENE GLYCOL BORATE ESTER.

| EXAMPLE | AMINE USED | MOLE RATIO, AMINE: BORATE ESTER | WT. RATIO, QUAT: FREE AMINE |
|---|---|---|---|
| 11 | di(hydrogenated tallow)amine | 1:1 | 65.5:21.4 |
| 12 | cocoamine | 1:0.75 | 48.5:25.3 |
| 13 | di(hydrogenated tallow)amine | 1:0.50 | 57.2:40.1 |
| 14 | tallowamine | 1:0.25 | 27.4:67.6 |

EXAMPLE 15

320 grams (2.0 gram moles) of the propylene glycol borate ester prepared in accordance with the procedures set forth in the first paragraph of Example 3 hereinabove were blended with 178.3 grams (2.0 gram moles) of dimethylethanolamine and 35.7 grams of diethylene glycol, a solvent. After heating the reaction mixture to 75° C., 176.0 grams (4.0 gram moles) of ethylene oxide were added to the mixture over the next 6 hours 5 minutes. The resulting mixture proved upon analysis to contain 0.34% water, and an ethoxylated quaternary ammonium propylene glycol borate ester having the formula:

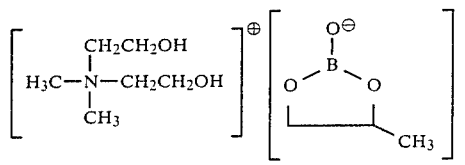

(XVI)

EXAMPLE 16

160 grams (1.0 gram mole) of the propylene glycol borate ester prepared in accordance with the procedures set forth in the first paragraph of Example 3 hereinabove were blended with 178.3 grams (2.0 gram moles) of dimethylethanolamine and 81.6 grams of diethylene glycol, a solvent. After heating the 16.1% (wt.) solvent-containing reaction mixture to 75° C., 88.0 grams (2.0 gram moles) of ethylene oxide were added to the mixture over the next 3 hours 20 minutes. The resulting mixture proved upon analysis to contain 0.05% water and the quaternary shown at Example 15.

EXAMPLE 17

In contrast to the above procedures, 74 grams (1.19 gram moles) of boric acid ($H_3BO_3$) was blended with 250 grams (0.95 gram moles) of Armeen®TMD and 100 grams of 2-ethylhexanol, a solvent. After heating the reaction mixture to 75° C., 209.2 grams of (4.75 gram moles) of ethylene oxide are added thereto over the next 12 hours 20 minutes. The resulting mixture proved upon analysis to contain 9.02% water. After 14 hours of distillation, this compound had a moisture content well in excess of 0.1%.

The manufacture of polyisocyanurate foams generally require catalysts, such as alkali metal salts, for the reaction to proceed normally. Surprisingly, the addition of the present compounds as co-polyols in polyisocyanurate and polyurethane foam manufacture eliminates the need for conventional catalysts. Further, the hydroxyl content of the present compounds reduces the need for a conventional polyol.

EXAMPLE 18

Thirteen (13.0) grams of the ethoxylated quaternary ammonium compound manufactured in accordance with the procedures at Example 12 were added to 120 grams of Voranol 575, a polyether polyol available from the Dow Chemical Company, Midland, Mich.; 2.7 grams of DC-193, a surfactant having silicone glycol copolymers with direct silicone-carbon bonds, and sold by the Dow Corning Corporation, Midland, Mich.; 54.0 grams of Freon 11A, a trifluorochloromethane available from E. I. DuPont de Nemours Company, Wilmington, De.; and 210 grams of Mondur MR, a polycyclic aromatic polyisocyanate available from the Mobay Chemical Corporation, Pittsburgh, Pa., and a polyurethane foam resulted. The blend had an NCO/OH ratio of 1.07, a cream time of 18 seconds, a gel time of 30 seconds, a rise time of 33 seconds, and a tack-free time of 37 seconds. No conventional catalyst was needed or used, and the resulting foam exhibited good physical properties.

EXAMPLE 19

Six and seven-tenths (6.7) grams of the ethoxylated quaternary ammonium compound manufactured by substituting tallowamine for the cocoamine in Example 12 were added to 126.3 grams of Voranol 575, 2.7 grams of DC-193, 54.0 grams of Freon 11A, and 213.9 grams of Mondur MR, and a polyurethane foam resulted. The blend had an NCO/OH ratio of 1.05, a cream time of 27 seconds, a gel time of 55 seconds, a rise time of 1 minute, and a tack-free time of 63 seconds. No conventional catalyst was needed or used, and the resulting foam exhibited good physical properties.

EXAMPLE 20

Thirteen (13.0) grams of the ethoxylated quaternary ammonium compound of Example 19 were added to 120 grams of Voranol 575, 2.7 grams of DC-193, 54.0 grams of Freon 11A, and 212.9 grams of Mondur MR, and a polyurethane foam resulted. The blend had an NCO/OH ratio of 1.05, a cream time of 22 seconds, a gel time of 37 seconds, a rise time of 39 seconds, and a tack-free time of 44 seconds. No conventional catalyst was needed or used, and the resulting foam exhibited good physical properties.

EXAMPLE 21

Six and seven-tenths (6.7) grams of the ethoxylated quaternary ammonium compound manufactured by substituting tallowamine for the di(hydrogenated tallow)amine in Example 13 were added to 126.3 grams of Voranol 575, 2.7 grams of DC-193, 54.0 grams of Freon 11A, and 212.9 grams of Mondur MR, and a polyurethane foam resulted. The blend had an NCO/OH ratio of 1.05, a cream time of 31 seconds, a gel time of 58 seconds, a rise time of 62 seconds, and a tack-free time of 72 seconds. No conventional catalyst was needed or used, and the resulting foam exhibited good physical properties.

EXAMPLE 22

Thirteen (13.0) grams of the ethoxylated quaternary ammonium compound of Example 21 were added to 120 grams of Voranol 575, 2.7 grams of DC-193, 54.0 grams of Freon 11A, and 210.7 grams of Mondur MR, and a polyurethane foam resulted. The blend had an NCO/OH ratio of 1.05, a cream time of 24 seconds, a gel time of 40 seconds, a rise time of 41 seconds, and a tack-free time of 50 seconds. No conventional catalyst was needed or used, and the resulting foam exhibited good physical properties.

EXAMPLE 23

Six and seven-tenths (6.7) grams of the ethoxylated quaternary ammonium compound manufactured in accordance with the procedures at Example 14 were added to 126.3 grams of Voranol 575, 2.7 grams of DC-193, 54.0 grams of Freon 11A, and 210 grams of Mondur MR, and a polyurethane foam resulted. The blend had an NCO/OH ratio of 1.08, a cream time of 31 seconds, a gel time of 62 seconds, a rise time of 66 seconds, and a tack-free time of 81 seconds. No conventional catalyst was needed or used, and the resulting foam exhibited good physical properties.

EXAMPLE 24

Thirteen (13.0) grams of the ethoxylated quaternary ammonium compound of Example 14 were added to 120 grams of Voranol 575, 2.7 grams of DC-193, 54.0 grams of Freon 11A, and 209 grams of Mondur MR, and a polyurethane foam resulted. The blend had an NCO/OH ratio of 1.09, a cream time of 24 seconds, a gel time of 48 seconds, a rise time of 52 seconds, and a tack-free time of 62 seconds. No conventional catalyst was needed or used, and the resulting foam exhibited good physical properties.

EXAMPLE 25

Six and seven-tenths (6.7) grams of the ethoxylated quaternary ammonium compound manufactured in accordance with the procedures at Example 10 were added to 120.3 grams of Voranol 575, 2.7 grams of DC-193, 54.0 grams of Freon 11A, and 210 grams of Mondur MR, and a polyurethane foam resulted. The blend had an NCO/OH ratio of 1.05, a cream time of 29 seconds, a gel time of 46 seconds, a rise time of 49 seconds, and a tack-free time of 54 seconds. No conventional catalyst was needed or used, and the resulting foam exhibited good physical properties.

EXAMPLE 26

Thirteen (13.0) grams of the ethoxylated quaternary ammonium compound manufactured in accordance with the procedures at Example 12 were added to 120 grams of Voranol 575, 2.7 grams of DC-193, 54.0 grams of freon 11A, and 210 grams of Mondur MR, and a polyurethane foam resulted. The blend had an NCO/OH ratio of 1.05, a cream time of 19 seconds, a gel time of 27 seconds, a rise time of 28 seconds, and a tack-free time of 35 seconds. No. conventional catalyst was needed or used, and the resulting foam exhibited good physical properties.

What we claim is:

1. A quaternary ammonium compound having the formula:

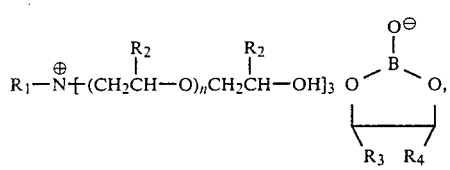

wherein $R_1$ is a straight- or branched-chain alkyl or alkenyl radical having from 1 to 30 carbon atoms, inclusive, or a phenyl or benzyl radical; $R_2$ is H—, a $C_1$ to $C_{10}$ straight- or branched-chain alkyl or alkenyl radical, a phenyl group, a benzyl group, or a halogenated alkyl group; $R_3$ and $R_4$ are different or the same and are selected from the group including H—, or a $C_1$ to $C_{10}$ straight- or branched-chain alkyl or alkenyl radical, a phenyl group, or a benzyl group, and wherein n is an integer between 0 and 30 inclusive, said quaternary ammonium compound having a water content not greater than 1.2 percent.

2. The compound as set forth in claim 1, wherein $R_1$ is a straight- or branched-chain alkyl or alkenyl radical having from 8 to 18 carbon atoms, and $R_2$ is H—.

3. The compound as set forth in claim 1, wherein $R_3$ and $R_4$ are H—.

4. The compound as set forth in claim 1, wherein $R_3$ is H— and $R_4$ is CH—.

5. The compound as set forth in claim 3, wherein n is 0.

6. The compound as set forth in claim 4, wherein n is 0.

7. The compound as set forth in claim 5, wherein $R_1$ is $C_{18}H_{37}$—.

8. The compound as set forth in claim 6, wherein $R_1$ is $C_{12}H_{25}$—.

9. A quaternary ammonium compound having the formula:

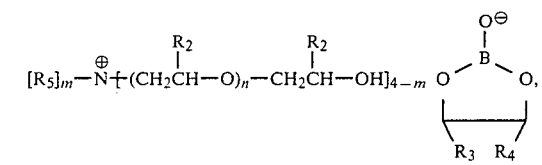

wherein m is either 0, 1, 2, or 3; each $R_5$ may be the same or different, and are selected from the groups including straight or branched-chain alkyl or alkenyl radical having from 1 to 30 carbon atoms, inclusive, or a phenyl or benzyl radical; $R_2$ is H—, a $C_1$ to $C_{10}$ straight- or branched-chain alkyl or alkenyl radical, a phenyl group, a benzyl group, or a halogenated alkyl group; $R_3$ and $R_4$ are different or the same and are selected from the group including H—, or a $C_1$ to $C_{10}$ straight- or branched-chain alkyl or alkenyl radical, a phenyl group, or a benzyl group, and wherein n is an integer between 0 and 30, inclusive, said quaternary ammonium compound having a water content not greater than 1.2 percent.

10. The compound as set forth in claim 9, wherein $R_5$ is a straight-chain alkyl radical having from 1 to 18 carbon atoms.

11. The compound as set forth in claim 10, wherein m is 2, and n is 0, and $R_2$ is H—.

12. The compound as set forth in claim 10, wherein m is 3, each $R_5$ is $CH_3CH_2$—, n is 0, and $R_2$ is $CH_3$—.

13. A quaternary ammonium compound having the formula:

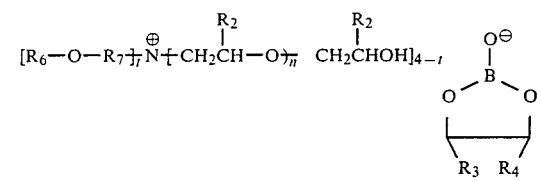

wherein t is either 1, 2, or 3, $R_2$ is H—, a $C_1$ to $C_{10}$ straight- or branched-chain alkyl or alkenyl radical, a phenyl group, a benzyl group, or a halogenated alkyl group; $R_3$ and $R_4$ are different or the same and are selected from the group including H—, or a $C_1$ to $C_{10}$ straight- or branched-chain alkyl or alkenyl radical, a phenyl group, or a benzyl group, n is an integer between 0 and 30, inclusive, $R_6$ is a $C_1$-$C_{20}$ alkyl or alkoxy group, and $R_7$ is a $C_2$ or $C_3$ alkyl group, said quaternary ammonium compound having a water content not greater than 1.2 percent.

14. The compound as set forth in claim 13, wherein $R_7$ is —$C_3H_6$— and $R_6$ is a combination of approximately equal amounts of $C_{12}$-$C_{15}$ alkyl groups.

15. A quaternary ammonium compound having the formula:

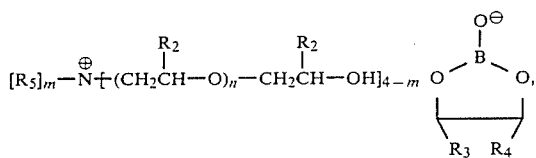

wherein m is either 0, 1, 2, or 3; each $R_5$ may be the same or different, and are selected from the groups including straight or branched-chain alkyl or alkenyl radical having from 1 to 30 carbon atoms, inclusive, or a phenyl or benzyl radical; $R_2$ is H—, a $C_1$ to $C_{10}$ straight- or branched-chain alkyl or alkenyl radical, a phenyl group, a benzyl group, or a halogenated alkyl group; $R_3$ and $R_4$ are different or the same and are selected from the group including H—, or a $C_1$ to $C_{10}$ straight- or branched-chain alkyl or alkenyl radical, a phenyl group, or a benzyl group, and wherein n is an integer between 0 and 30, inclusive made by the process of claim 14.

16. The compound as set forth in claim 15, wherein $R_5$ is a straight-chain alkyl radical having from 1 to 18 carbon atoms.

17. The compound as set forth in claim 16, wherein m is 2, and n is 0, and $R_2$ is H—.

18. The compound as set forth in claim 16, wherein m is 3, each $R_5$ is $CH_3CH_2$—, n is 0, and $R_2$ is $CH_3$.

19. The compound of claim 1 containing less than about 0.1 percent water.

20. The compound of claim 9 containing less than about 0.1 percent water.

21. The compound of claim 13 containing less than about 0.1 percent water.

22. A method of making an ethoxylated quaternary ammonium glycol borate ester, comprising blending boric acid with an alkylene glycol so as to form an alkylene glycol borate ester; removing the majority of water from said alkylene glycol borate ester so that water remaining therein does not exceed 0.2% of the total weight of said alkylene glycol borate ester and said water; adding said alkylene glycol borate ester to a primary, secondary, or tertiary amine so as to form an aminated alkylene glycol borate ester; and alkoxylating said aminated alkylene glycol borate ester with an alkylene oxide in the presence of a solvent.

23. A method of making an ethoxylated quaternary ammonium glycol borate ester, comprising blending boric acid with an alkylene glycol and heating the blend so as to form an alkylene glycol borate ester; removing the majority of water from said alkylene glycol borate ester; adding said alkylene glycol borate ester to a primary, secondary, or tertiary amine so as to form an aminated alkylene glycol borate ester; and alkoxylating said aminated alkylene glycol borate ester with an alkylene oxide in the presence of a solvent.

24. The method as set forth in claim 23, wherein the molar ratio of said alkylene glycol to boric acid is between 1:1 and 3:1.

25. The method as set forth in claim 23, wherein said solvent comprises from 5%–20% of the combined weight of said solvent, boric acid, alkylene glycol, amine, and alkylene oxide.

26. The method as set forth in claim 23, wherein said solvent comprises from 5%–20% of the combined weight of said solvent, boric acid, alkylene glycol, amine, and alkylene oxide.

27. The method as set forth in claim 23, wherein the molar ratio of said amine to said alkylene glycol borate ester is 1:0.75.

28. The method as set forth in claim 23, wherein the molar ratio of said amine to said alkylene glycol borate ester is 1:0.50.

29. The method as set forth in claim 26, wherein the molar ratio of said amine to said alkylene glycol borate ester is 1:0.75.

30. The method as set forth in claim 26, wherein the molar ratio of said amine to said alkylene glycol borate ester is 1:0.50.

31. The method as set forth in claim 30, wherein said solvent is diethylene glycol.

32. The method as set forth in claim 30, wherein said solvent is ethylene glycol.

* * * * *